United States Patent [19]

Nickel et al.

[11] Patent Number: 5,068,242
[45] Date of Patent: Nov. 26, 1991

[54] PYRROLIDINE-2-CARBOXYLIC ACID DERIVATIVES AND THEIR USE FOR PSYCHOTROPIC ACTION

[75] Inventors: Wolf-Ulrich Nickel, Bad Soden am Taunus; Wolfgang Rüger, Kelkheim; Hansjörg Urbach, Kronberg/Taunus; Franz Hock, Dieburg, all of Fed. Rep. of Germany

[73] Assignee: Hoechst Aktiengesellschaft, Frankfurt am Main, Fed. Rep. of Germany

[21] Appl. No.: 437,890

[22] Filed: Nov. 17, 1989

[30] Foreign Application Priority Data

Nov. 19, 1988 [DE] Fed. Rep. of Germany ....... 3839127

[51] Int. Cl.$^5$ ................... C07D 209/52; A61K 31/40
[52] U.S. Cl. ..................................... 514/412; 548/452
[58] Field of Search ........................ 548/452; 514/412

[56]     References Cited
U.S. PATENT DOCUMENTS
4,668,796  5/1987  Geiger et al. ................. 548/452

Primary Examiner—David B. Springer
Attorney, Agent, or Firm—Finnegan, Henderson, Farabow, Garrett, and Dunner

[57] ABSTRACT

The present invention relates to compounds of the formula I

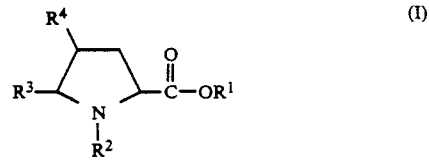

in which $R^1$ to $R^4$ are defined in the description, processes for their preparation, their use for the treatment and prophylaxis of cognitive dysfunctions and pharmaceuticals containing them and processes for their preparation.

4 Claims, No Drawings

PYRROLIDINE-2-CARBOXYLIC ACID DERIVATIVES AND THEIR USE FOR PSYCHOTROPIC ACTION

DESCRIPTION

The invention relates to new pyrrolidine-2-carboxylic acid derivatives, agents containing them and their use as pharmaceuticals having a psychotropic action for the treatment and prophylaxis of disorders in the central nervous system, in particular having a nootropic action for the treatment of cognitive dysfunctions.

The object of the invention is to find new compounds which have an antiamnesic action.

This object is achieved according to the invention by the compounds of the formula I

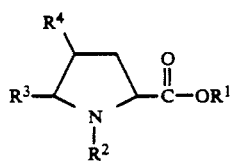

in which $R^1$ is
hydrogen,
a substituted or unsubstituted aliphatic radical having 1–18 carbon atoms,
a substituted or unsubstituted alicyclic radical having 3–20 carbon atoms,
a substituted or unsubstituted alicyclic-aliphatic radical having 4–20 carbon atoms,
a substituted or unsubstituted aromatic radical having 6–12 carbon atoms,
a substituted or unsubstituted araliphatic radical having 7–32 carbon atoms,
a substituted or unsubstituted heteroaromatic or heteroaromatic-$C_1$-$C_8$-aliphatic radical having 5–12 ring atoms, $R^2$ is
hydrogen,
a substituted or unsubstituted aliphatic radical having 1–21 carbon atoms,
a substituted or unsubstituted alicyclic radical having 3–20 carbon atoms,
a substituted or unsubstituted alicyclic-aliphatic radical having 4–20 carbon atoms,
a substituted or unsubstituted aromatic radical having 6–12 carbon atoms,
a substituted or unsubstituted araliphatic radical having 7–32 carbon atoms,
a substituted or unsubstituted heteroaromatic or heteroaromatic-$C_1$-$C_8$-aliphatic radical having 5–12 ring atoms,
a substituted or unsubstituted alkanoyl radical having 1–18 carbon atoms,
a substituted or unsubstituted $C_3$-$C_8$-cycloalkyl-$C_1$-$C_8$-alkanoyl radical,
a substituted or unsubstituted $C_7$-$C_{13}$-aroyl radical,
a substituted or unsubstituted $C_6$-$C_{12}$-aryl-$C_1$-$C_{18}$-alkanoyl radical,
a substituted or unsubstituted $C_7$-$C_{13}$-aroyl-$C_1$-$C_{18}$-alkanoyl radical or
a substituted or unsubstituted $C_1$-$C_{10}$-alkoxycarbonyl radical, $R^3$ is
a substituted or unsubstituted aliphatic radical having 1–18 carbon atoms,
a substituted or unsubstituted alicyclic radical having 3–20 carbon atoms,
a substituted or unsubstituted aromatic radical having 6–12 carbon atoms or
a substituted or unsubstituted araliphatic radical having 7–32 carbon atoms, $R^4$ is
a substituted or unsubstituted aliphatic radical having 1–18 carbon atoms,
a substituted or unsubstituted alicyclic radical having 3–20 carbon atoms,
a substituted or unsubstituted alicyclic-aliphatic radical having 4–20 carbon atoms,
a substituted or unsubstituted aromatic radical having 6–12 carbon atoms,
a substituted or unsubstituted araliphatic radical having 7–32 carbon atoms,
a substituted or unsubstituted heteroaromatic or heteroaromatic-$C_1$-$C_8$-aliphatic radical having 5–12 ring atoms, but is not hydrogen,
or $R^4$ together with the carbon atom which carries this substituent forms a spiro-linked mono- or bicyclic ring system of 3–8 carbon atoms,
or $R^3$ and $R^4$ together with the atoms which carry them form a substituted or unsubstituted mono- or bicyclic ring system of 3–8 carbon atoms, with the exception of compounds in which at the same time $R_1$ is hydrogen, benzyl or n-octyl, $R^2$ is tert.-butoxycarbonyl and $R^3$ and $R^4$ together with the atoms which carry them are a cyclopentane or cyclopentene ring, and compounds in which $R^2$ is substituted or unsubstituted α-amino-$C_1$-$C_6$-alkanoyl.

A substituted or unsubstituted aliphatic radical is understood to mean an aliphatic acyclic radical, i.e. a radical having an open, straight or branched carbon chain, such as, for example, alkyl, alkenyl, alkynyl and the corresponding polyunsaturated radicals. It is preferably unsubstituted or monosubstituted, for example by hydroxyl, alkoxy, halogen, amino, alkanoylamino, alkoxycarbonylamino, arylalkoxycarbonylamino, arylalkylamino, alkylamino, dialkylamino, alkylthio, arylthio, carboxyl, carbamoyl, alkoxycarbonyl, alkanoyloxy, alkoxycarbonyloxy, aryloxy or aryloxycarbonyloxy.

A substituted or unsubstituted alicyclic radical and the corresponding substituted or unsubstituted alicyclic-aliphatic radical which is linked via an open carbon chain is a preferably mono- to pentacyclic isocyclic nonaromatic radical having single or double bonds which are distributed unsymmetrically and can also be branched (i.e. can carry open-chain aliphatic side chains) and is linked via a ring carbon atom or a side chain carbon atom. It is preferably unsubstituted. Several rings as components of such a radical are fused, spiro-linked or isolated. Examples of these radicals are cycloalkyl, cycloalkenyl, cycloalkylalkyl, bicycloalkyl, tricycloalkyl and radicals derived from mono-, bi- or oligocyclic terpenes, such as menthyl, isomenthyl, bornanyl, bornyl, caranyl, epibornyl, epiisobornyl, isobornyl, menthanyl, neomenthyl, neoisomenthyl, pinanyl, thujanyl; they are preferably unsubstituted (aliphatic side chains do not represent substituents by the present definition).

A substituted or unsubstituted aromatic radical is preferably aryl such as phenyl, biphenylyl or naphthyl, which is unsubstituted or mono-, di- or trisubstituted as mentioned in page 6 for aryl. Radicals which are derived from aryl, such as aralkyl, aryloxy, arylthio or aroyl, preferably benzoyl, can be substituted like aryl.

A substituted or unsubstituted heteroaromatic radical is ; preferably an aromatic mono- or bicyclic heterocyclic radical having 5 to 7 or 8 to 12, preferably up to 10, ring atoms, 1 to 2 ring atoms of which are sulfur or oxygen atoms and/or 1 to 4 ring atoms of which are nitrogen atoms, such as, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated. A heteroaromatic radical and the corresponding heteroaromaticaliphatic radical can be substituted as defined below.

A substituted or unsubstituted araliphatic radical is understood to mean in particular aralkyl radicals such as arylalkyl, diarylalkyl, indanyl or fluorenyl in which aryl is defined as below and can be substituted in the manner mentioned there.

$R^3$ and $R^4$ together with the atoms carrying them can form a mono- or bicyclic alicyclic or aromatic ring system having 3-8 carbon atoms. Suitable ring systems are: cyclopropane, cyclobutane, cyclopentane, cyclohexane, cycloheptane, cyclooctane, norbornane, bicyclo[2.2.2]octane, bicyclo[3.2.1]octane, benzene, which can be partially unsaturated and/or substituted.

In the case that $R^4$ together with the atom carrying this substituent forms a spiro-linked mono- or bicyclic ring system, suitable monocyclic substituents are alicyclic or heterocyclic ring systems having 3-8 atoms in which up to 2 oxygen atoms or up to 2 sulfur atoms or one nitrogen atoms can be present and suitable bicyclic substituents are preferably alicyclic ring systems having 5-9 atoms.

Suitable compounds of the formula I which have several chiral atoms are all possible diastereomers in the form of racemates or enantiomers or mixtures of different diastereomers. However, preference is given to the compounds of the formula I in which the chiral carbon atoms have S configurations.

A preferred embodiment is identified by compounds of the formula I in which
$R^1$ is
hydrogen;
$C_1$-$C_{18}$-alkyl,
an aliphatic acyclic radical of the formula $C_aH_{(2a+b-1)}$ in which double bonds, if their number exceeds 1, are not cumulated, a is an integer from 2 to 18 and b an integer from 2 to a;
a mono-, di- or tricyclic nonaromatic straight-chain or branched hydrocarbon radical of the formula $C_cH_{(2c-d-1)}$ in which c is an integer from 3 to 20 and d an integer from 0 to (c-2);
$C_6$-$C_{12}$-aryl which can be mono-, di- or trisubstituted by $C_1$-$C_8$-alkyl, $C_1$-$C_4$-alkoxy, hydroxyl, halogen, nitrile, amino, aminomethyl, $C_1$-$C_4$-alkylamino, di-$C_1$-$C_4$-alkylamino, $C_1$-$C_4$-alkanoylamino, methylenedioxy, carboxyl, cyano and/or sulfoamoyl;
amino-$C_1$-$C_8$-alkyl;
$C_1$-$C_4$-alkanoylamino-$C_1$-$C_8$-alkyl;
$C_7$-$C_{13}$-aroylamino-$C_1$-$C_8$-alkyl;
$C_1$-$C_4$-alkoxycarbonylamino-$C_1$-$C_8$-alkyl;
$C_6$-$C_{12}$-aryl-$C_1$-$C_4$-alkoxycarbonylamino-$C_1$-$C_8$-alkyl;
$C_6$-$C_{12}$-aryl-$C_1$-$C_4$-alkylamino-$C_1$-$C_8$-alkyl;
$C_1$-$C_4$-alkylamino-$C_1$-$C_8$-alkyl;
di-$C_1$-$C_4$-alkylamino-$C_1$-$C_8$-alkyl;
guanidino-$C_1$-$C_8$-alkyl;
$C_1$-$C_4$-alkylthio-$C_1$-$C_8$-alkyl;
$C_6$-$C_{12}$-arylthio-$C_1$-$C_8$-alkyl or $C_6$-$C_{12}$-aryloxy-$C_1$-$C_8$-alkyl which can both be substituted in the aryl moiety as described above;
carboxy-$C_1$-$C_{17}$-alkyl, $C_1$-$C_4$-alkoxycarbonyl-$C_1$-$C_{17}$-alkyl, carbamoyl-$C_1$-$C_{17}$-alkyl, $C_1$-$C_4$-mono- or dialkylcarbamoyl
-$C_1$-$C_{17}$-alkyl in which alkyl is unsubstituted or substituted by $C_6$-$C_{12}$-aryl;
$R^2$ is
hydrogen;
$C_1$-$C_{18}$-alkyl;
an aliphatic acyclic radical of the formula $C_aH_{(2a-b+1)}$ in which double bonds, if their number exceeds 1, are not cumulated, a is an integer from 2 to 18 and b is an integer from 2 to a;
a mono-, bi- or tricyclic nonaromatic straight-chain or branched hydrocarbon radical of the formula $C_cH_{(2c-d-1)}$ in which c is an integer from 3 to 20 and d is an even number from 0 to (c-2);
$C_6$-$C_{12}$-aryl;
$C_6$-$C_{12}$-aryl-$C_1$-$C_8$-alkyl or $C_7$-$C_{13}$-aroyl-$C_1$-$C_8$-alkyl which can substituted in the aryl moiety as described above;
mono- or bicyclic, optionally partially hydrogenated heteroaryl or heteroaryl-$C_1$-$C_8$-alkyl having 5-7 or 8-10 ring atoms, up to 9 ring atoms of which are carbon and 1 to 2 ring atoms are sulfur or oxygen and/or 1 to 4 ring atoms are nitrogen, which can be substituted in the heteroaryl moiety as described above for aryl;
$C_1$-$C_{18}$-alkanoyl;
$C_6$-$C_{12}$-aryl-$C_1$-$C_8$-alkanoyl which can be substituted in the aryl moiety as described above,
$C_7$-$C_{13}$-aroyl-$C_1$-$C_8$-alkanoyl which can be substituted in the aryl moiety as described above,
$C_1$-$C_6$-alkoxycarbonyl-$C_1$-$C_8$-alkanoyl,
$C_6$-$C_{12}$-aryloxycarbonyl-$C_1$-$C_8$-alkanoyl which can be substituted in the aryl moiety as described above;
$C_6$-$C_{12}$-aryl-$C_1$-$C_8$-alkoxycarbonyl;
$C_1$-$C_6$-alkoxy-$C_1$-$C_6$-alkanoyl,
$C_6$-$C_{12}$-aryloxy-$C_1$-$C_6$-alkanoyl which can be substituted in the aryl moiety as described above for aryl,
$C_1$-$C_6$-acyl-$C_1$-$C_8$-alkanoyl,
carboxy-$C_1$-$C_4$-alkanoyl,
carbamoyl-$C_1$-$C_4$-alkanoyl,
amino-$C_1$-$C_4$-alkyl;
$C_1$-$C_4$-alkanoylamino-$C_1$-$C_4$-alkyl;
$C_7$-$C_{13}$-aroylamino-$C_1$-$C_4$-alkyl;
$C_1$-$C_4$-alkoxycarbonylamino-$C_1$-$C_4$-alkyl;
$C_6$-$C_{12}$-aryl-$C_1$-$C_4$-alkoxycarbonylamino-$C_1$-$C_4$-alkyl;
$C_6$-$C_{12}$-aryl-$C_1$-$C_4$-alkylamino-$C_1$-$C_4$-alkyl;
$C_1$-$C_4$-alkylamino-$C_1$-$C_4$-alkyl;
di-$C_1$-$C_4$-alkylamino-$C_1$-$C_4$-alkyl;
guanidino-$C_1$-$C_4$-alkyl;
$C_1$-$C_4$-alkylthio-$C_1$-$C_4$-alkyl;
$C_6$-$C_{12}$-arylthio-$C_1$-$C_4$-alkyl which can be substituted in the aryl moiety as described above;
carboxy-$C_1$-$C_4$-alkyl; carbamoyl-$C_1$-$C_4$-alkyl;
$C_1$-$C_4$-alkoxycarbonyl-$C_1$-$C_4$-alkyl;
$C_6$-$C_{12}$-aryloxy-$C_1$-$C_4$-alkyl which can be substituted in the aryl moiety as described above for aryl, and R³ and R⁴ together with the atoms carrying them form a substituted or unsubstituted mono- or bicyclic ring system of 3-8 carbon atoms, with the exception of compounds in which at the same time R¹ is hydrogen, benzyl or n-octyl, R² is tert.-butoxycarbonyl and R³ and R⁴ together with the atoms carrying them are the cyclopentane or cyclopentene ring.

In particular those compounds of the formula I are suitable in which

R¹ is
hydrogen; $C_1$-$C_8$-alkyl; $C_2$-$C_6$-alkenyl; $C_3$-$C_9$-cycloalkyl; amino-$C_1$-$C_4$-alkyl; $C_2$-$C_5$-acylamino-$C_1$-$C_4$-alkyl; $C_7$-$C_{13}$-aroylamino-$C_1$-$C_4$-alkyl; $C_1$-$C_4$-alkoxycarbonylamino -$C_1$-$C_4$-alkyl; $C_1$-$C_4$-alkoxycarbonyl-$C_1$-$C_{10}$-alkyl; carbamoyl-$C_1$-$C_{10}$-alkyl; $C_1$-$C_4$-mono- or -dialkylcarbamoyl -$C_1$-$C_{10}$-alkyl; in which alkyl is unsubstituted or substituted by phenyl;

$C_6$-$C_{12}$-aryl-$C_1$-$C_6$-alkyl;

$C_6$-$C_{12}$-aryl-$C_1$-$C_4$-alkoxycarbonylamino-$C_1$-$C_4$-alkyl;

$C_6$-$C_{12}$-aryl which can be mono-, di- or trisubstituted by $C_1$-$C_4$-alkyl, $C_1$-$C_4$-alkoxy, hydroxyl, halogen, nitro, amino, $C_1$-$C_4$-alkylamino, di-$C_1$-$C_4$-alkylamino and/or methylenedioxy;

in particular hydrogen, methyl, ethyl, octyl, benzyl, benzhydryl, tert.-butoxycarbonylamino-$C_1$-$C_4$alkyl, -alkyl, benzyloxycarbonylamino-$C_1$-$C_4$-alkyl, carboxy-$C_1$-$C_{10}$-alkyl; $C_1$-$C_4$-alkoxycarbonyl-$C_1$-$C_{10}$-alkyl;

R² is
hydrogen;
$C_1$-$C_6$-alkyl which can be unsubstituted or substituted by amino, $C_1$-$C_6$-acylamino or benzoylamino; $C_2$-$C_6$-alkenyl, $C_3$-$C_9$-cycloalkyl, $C_5$-$C_9$-cycloalkenyl, $C_3$-$C_7$-cycloalkyl-$C_1$-$C_4$-alkyl, $C_6$-$C_{12}$-aryl or partially hydrogenated aryl, each of which can be substituted by $C_1$-$C_4$-alkyl, $C_1$- or $C_2$-alkoxy or halogen;

$C_6$-$C_{12}$-aryl-$C_1$-$C_6$-alkyl or $C_7$-$C_{13}$-aroyl-$C_1$-$C_4$-alkyl, both of which can be substituted in the aryl moiety as defined above;

$C_1$-$C_8$-alkanoyl;

$C_6$-$C_{12}$-aryl-$C_1$-$C_6$-alkanoyl which can be substituted in the aryl moiety as defined above;

$C_1$-$C_4$-alkoxycarbonyl-$C_1$-$C_7$-alkanoyl;

$C_6$-$C_{12}$-aryloxycarbonyl-$C_1$-$C_7$-alkanoyl which can be substituted in the aryl moiety as defined above;

$C_1$-$C_4$-acyl-$C_2$-$C_6$-alkanoyl;

$C_1$-$C_4$-acylamino-$C_1$-$C_6$-alkanoyl;

$C_7$-$C_{13}$-aroyl-$C_1$-$C_6$-alkanoyl which can be substituted in the aryl moiety as defined above; but in particular hydrogen, $C_1$-$C_6$-alkanoyl, $C_6$-$C_{12}$-aryl-$C_1$-$C_6$-alkanoyl, $C_7$-$C_{13}$-aroyl-$C_1$-$C_3$-alkanoyl, tert.-butoxycarbonyl, benzyloxycarbonyl, tert.-butoxycarbonylamino-$C_2$-$C_3$-alkanoyl, benzyloxycarbonylamino-$C_2$-$C_3$-alkanoyl, $C_6$-$C_{12}$-aryl-$C_1$-$C_3$-acylamino-$C_2$-$C_3$-alkanoyl, trifluoroacetylamino-$C_2$-$C_3$-alkanoyl;

R³ and R⁴ together with the atoms carrying them form a monocyclic alicyclic or aromatic ring system, in particular cyclopentane, cyclopentene, cyclohexane, cyclooctane and benzene, with the exception of compounds in which at the same time R¹ is hydrogen, benzyl or n-octyl, R² is tert.-butoxycarbonyl and R³ and R⁴ together with the atoms carrying them form a cyclopentane or cyclopentene ring and compounds in which R² is α-acylamino-$C_1$-$C_6$-alkanoyl.

The invention furthermore relates to a process for the preparation of a compound of the formula I, which comprises reacting its fragments in a suitable solvent in the absence or presence of a base and/or a coupling aid with one another, reducing any unsaturated compounds which may be formed as intermediates, such as Schiff bases, eliminating protective groups which have been introduced temporarily for the protection of reactive groups, if appropriate esterifying compounds of the formula I which contain free carboxyl group(s) and, if appropriate, converting the compounds obtained into their physiologically acceptable salts.

For example, compounds of the formulae II and III

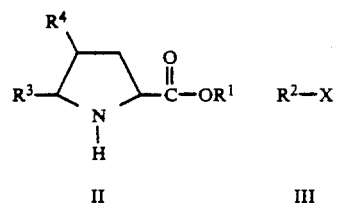

can be reacted in the manner mentioned to give compounds in which R¹ to R⁴ are as defined above and X, in the case of alkylations, is a suitable leaving group, in particular halogen, $C_1$-$C_4$-alkylsulfonyloxy, arylsulfonyloxy, and, in the case of acylations, hydroxyl, $C_1$-$C_3$-alkoxy, $C_6$-$C_{12}$-aryloxy, $C_6$-$C_{12}$-aryl-$C_1$-$C_6$-alkoxy or the radical of an activated acid derivative.

The reaction of these compounds can be carried out, for example in analogy to known peptide coupling processes, in an organic solvent such as DMF, $CH_2Cl_2$, DMA in the presence of coupling aids, such as carbodiimides (e.g. dicyclohexylcarbodiimide), diphenylphosphorylazide, alkanephosphoric anhydrides, dialkylphosphinic anhydrides or N,N-succinimidyl carbonates in a solvent such as $CH_3CN$. Amino groups in compounds of the formula II can be activated by means of tetraethyl diphosphite. The compounds of the formula III can be converted into active esters (e.g. by means of 1-hydroxybenzotriazole), mixed anhydrides, (e.g. by means of chloroformic esters), azides or carbodiimide derivatives and thus become activated (cf. Houben-Weyl, Meth. d. organ. Chemie (Methods of Organic Chemistry) vol. XV 1 and 2). The reaction is preferably carried out between −20° C. and the boiling point of the reaction mixture.

However, the reaction to give the compounds of the formula I can also be carried out thermally in a suitable organic solvent in the temperature range between 0° C. and the boiling point of the solvent.

The preparation of the new compounds of the general formula I can also be effected by using alkylation methods or esterification methods which are known to one skilled in the art, for example by reacting a compound of the formula I in which the radical R: is hydrogen with a suitable alkylating agent of the general formula R¹X in which X is as defined above, such as, for example, an alkyl halide, with basic catalysis in a polar protic or dipolar aprotic solvent, or for example by reacting a compound of the formula I, for example, with an aliphatic alcohol with acidic or basic catalysis in a polar protic or dipolar aprotic solvent.

The nootropic action of the compounds according to the invention were tested on mice which had a body weight of 20-25 g in the inhibitory (passive) avoidance test (step-through model). A modified form of the testing method described by J. KOPP, Z. BODANECKY and M. E. JARVIK has been described by J. BURES, O. BURESOVA and J. HUSTON in "Techniques and Basic Experiments for the Study of Brain and Behavior", Elsevier Scientific Publishers, Amsterdam (1983).

In accordance with these references, a substance is designated as having a nootropic action, if it is capable of removing amnesia generated in the test animals by means of an electroconvulsive shock or induced by means of scopolamine.

The tests were carried out according to modified tests methods. The known nootropic agent 2-oxo-1-pyrrolidinyl acetamide (Piracetam) served as comparison.

The substantial superiority of the compounds according to the invention over the comparison substance was shown by the fact that the scopolamine-induced amnesia can be removed in the inhibitory avoidance test at an MED (minimal effective dose) of 0.1-30 mg/kg p.o. The comparison substance has an MED of about 500-1,000 mg/kg p.o.

The compounds according to the invention in general have only low toxicity and, due to their pharmacological properties, are suitable for the treatment of cognitive dysfunctions of different genesis, such as are observed, for example, in Alzheimer,s disease or senile dementia.

Surprisingly, it has been found that the compounds of the formula I in which $R_2$ is the side chain, which, if necessary, may be protected, of a naturally occurring α-amino acid or is substituted or unsubstituted α-amino-$C_1$-$C_6$-alkanoyl, which compounds are already known as intermediates, and the compounds of the formula I in which at the same time $R^1$ is hydrogen, benzyl or n-octyl, $R^2$ is tert.-butoxycarbonyl and $R^3$ and $R^4$ together with the atoms carrying them are a cyclopentane or cyclopentene ring, which compounds are also already known as intermediates, have the same pharmacological properties in combination with lower toxicity. The present invention therefore also relates to these compounds of the formula I, which are already known as intermediates, as pharmacological active substances.

If $R^2$ is a side chain of a protected naturally occurring α-amino acid, such as, for example, protected Ser, Thr, Asp, Asn, Glu, Gln, Arg, Lys, Hyl, Cys, Orn, Cit, Tyr, Trp or His, the preferred protective groups are the groups customary in peptide chemistry (cf. Houben-Weyl, vol. XV/1 and XV/2). In the case that $R^2$ is the protected lysine side chain, the known amino-protecting groups, but in particular Z, Boc or $C_1$-$C_6$-alkanoyl, are preferred. Suitable O-protecting groups for tyrosine are preferably $C_1$-$C_6$-Alk, in particular methyl or ethyl.

Preferred side chains of naturally occurring α-amino acids are those of proteinogenic α-amino acids.

The invention furthermore comprises medicaments containing compounds of the formula I, processes for their preparation and the use of the compounds of the formula I for the preparation of medicaments which are used for the treatment and prophylaxis of the above-mentioned diseases.

The pharmaceuticals are prepared by processes which are known per se and known to one skilled in the art. As pharmaceuticals, the pharmacologically active compounds (=active substance) according to the invention are used either as such or preferably in combination with suitable pharmaceutical auxiliaries in the form of tablets, coated tablets, capsules, suppositories, emulsions, suspensions or solutions in which the active substance content is about 95%, advantageously between 10 and 75%.

Which auxiliaries are suitable for the desired pharmaceutical formulation, is known to one skilled in the art on the basis of his specialist knowledge. In addition to solvents, gel formers, suppository bases, tablet auxiliaries and other active substance carriers, for ; example antioxidants, dispersants, emulsifiers, antifoams, masking flavors, preservatives, solubilizing agents or colorants can be used.

The active substances can be administered for example orally, rectally or parenterally (e.g. intravenously or subcutaneously), oral administration being preferred. For an oral administration form, the active compounds are mixed with suitable additives such as excipients, stabilizers or inert diluents and converted into a suitable application form by conventional methods, such as tablets, coated tablets, hard gelatin capsules, aqueous, alcoholic or oily suspensions or aqueous, alcoholic or oily solutions. The inert excipients used can be, for example, gum arabic, magnesium, magnesium carbonate, lactose, glucose or starch, in particular corn starch. The preparation can take place not only as dry but also as moist granules. Oily excipients or solvents are, for example, oils of plant or animal origin such as sunflower oil or fish liver oil.

For subcutaneous or intravenous application, the active compounds or their physiologically acceptable salts, if desired in conjunction with customary substances such as solubilizers, emulsifiers or further auxiliaries, are made into a solution, suspension or emulsion. Examples of suitable solvents are water, physiological saline solution or alcohols, e.g. ethanol, propanol, glycerol, apart from them also sugar solutions such as glucose or mannitol solutions or even a mixture of the various solvents mentioned.

The examples below are intended to illustrate the invention without limiting it to the compounds mentioned:

EXAMPLE 1

Benzyl 2-N-(4-(2-naphthyl)butyryl)-(1S,3S,5S)-2-azabicyclo[3.3.0]octane-3-carboxylate 2 5 g of benzyl (1S,3S,5S)-2-azabicyclo[3.3.0]octane-3-carboxylate and 2.2 g of 4-(2-naphthyl)butyric acid are dissolved in 40 ml of DMF and cooled to $-5°$ C. 7.7 ml of triethylamine and then 10 ml of n-propylphosphonic anhydride (50 % strength solution in dichloromethane) were pipetted into this solution under a nitrogen atmosphere. This mixture was stirred at room temperature for 48 hours, to effect complete conversion. The solution was diluted with 100 ml of ethyl acetate and successively extracted two times each with saturated $NaHCO_3$ solution, 10 % strength citric acid solution and saturated NaCl solution. After drying over $MgSO_4$ and concentration of the organic phase, the crude product obtained was separated by column chromatography over silica gel (cyclohexane/ethyl acetate). This gave 2.52 g of the desired product.

$\alpha^{25}_D: -13.9°$ (c=1.01 in methanol).

The following compounds were prepared analogously to the procedure described in Example 1:

EXAMPLE 2

Benzyl 2-N-(5-phenylvaleryl)-(1S,3S,5S)-2=azabicyclo[3.3.]octane-3-carboxylate $\alpha^{25}_{D}$:−16.2° (c=1.18 in methanol).

EXAMPLE 3

Benzyl 2-N-(3-(2-naphthoyl)propionyl-(1S,3S,5S)-2-azabicyclo[3.3.0]octane-3-carboxylate $\alpha^{25}_{D}$:−20.3° (c=1.08 in methanol).

EXAMPLE 4

Benzyl 2-phenylacetyl-(1S,3S,5S)-2-azabicyclo[3.3.0]octane-3-carboxylate $\alpha^{25}_{D}$:−26.4° (c=1 in methanol).

EXAMPLE 5

Benzyl 2-(3-phenylpropionyl)-(1S,3S,5S)-2-azabicyclo[3.3.0]octane-3-carboxylate $\alpha^{25}_{D}$:−16.5° (c=1 in methanol).

EXAMPLE 6

Benzyl 2-(4-phenylbutyryl)-(1S,3S,5S)-2-azabicyclo[3.3.0]octane-carboxylate $\alpha^{25}_{D}$:−15.3° (c=1 in methanol).

EXAMPLE 7

Benzyl 2-(5-phenylhexanoyl)-(1S,3S,5S)-2-azabicyclo[3.3.0]octane-3-carboxylate $\alpha^{25}_{D}$:−12.6° (c=1 in methanol).

EXAMPLE 8

Benzyl 2-N-(N-trifluoroacetyl-S-alanyl)-(1S,3S,5S)-2-azabicyclo[3.3.0]octane-3-carboxylate $\alpha^{25}_{D}$:−64.9° (c=1.0 in methanol).
Melting point: 75-78° C.

EXAMPLE 9 n-Octyl 2-propionyl-(1S,3S,5S)-2-azabicyclo[3.3.0]octane-3-carboxylate $\alpha^{25}_{D}$:−8.4° (c=1 in methanol).

EXAMPLE 10 n-Ooctyl 2-tert.-butyloxycarbonyl-(1S,3S,5S)-2-azabicyclo[3.3.0]octane-3-carboxylate $\alpha^{25}_{D}$:+5.5° (c=2 in methanol).

EXAMPLE 11 n-Octyl 2-(6-phenylhexanoyl)-(1S,3S,5S)-2-azabicyclo[3.3.0]octane-3-carboxylate $\alpha^{25}_{D}$:−3.7° (c=2 in methanol

EXAMPLE 12 n-Octyl 2-[N-tert.-butyloxycarbonyl-S-alanyl]-(1S,3S,5S)-2-azabicyclo[3.3.0]octane-3-carboxylate $\alpha^{25}_{D}$:−39.9° (c=1 in methanol).

EXAMPLE 13 n-Octyl 2-[N-benzyloxycarbonyl-S-alanyl]-(1S,3S,5S)-2-azabicyclo[3.3.0]octane-3-carboxylate $\alpha^{25}_{D}$:−38.0° (c=1 in methanol).

EXAMPLE 14 n-Octyl 2-[N-(3-phenylpropionyl)-S-alanyl]-(1S,3S,5S)-2-azabicyclo[3.3.0]octane-3-carboxylate $\alpha^{25}_{D}$:−35.3° (c=1 in methanol).

EXAMPLE 15

2-N-(4-(2-naphthyl)-butyryl)-(1S,3S,5S)-2-azabicyclo[3.3.0]octane-3-carboxylic acid 2 g of the benzyl ester described in Example 1 were dissolved in 60 ml of absolute ethanol and hydrogenated catalytically on palladium/carbon at room temperature. After the reaction was completed, the catalyst was removed by filtration, and the filtrate was freed from solvent in vacuo. 1.52 g of product were obtained as an amorphous powder.

$\alpha^{25}_{D}$:+14.2° (c=1.06 in methanol).

The following compounds of Examples 16–19 were prepared analogously t the procedure given in Example 15:

EXAMPLE 16

Dicyclohexylammonium 2-N-(5-phenylvaleryl)-(1S,3S,5S)-2-azabicyclo[3.3.0]octane-3-carboxylate The benzyl ester described in Example 2 was treated as in Example 15, the carboxylic acid obtained was dissolved in diisopropyl ether and precipitated as dicyclohexylammonium salt.

$\alpha^{20}_{D}$:+18.7° (c=1.04 in methanol).
Melting point: 113° C.

EXAMPLE 17

2-N-(3-(2-naphthoyl)propionyl)-(1S,3S,5S)-2-azabicyclo[3.3.0]octane-3-carboxylic acid Melting point: 147° C.

EXAMPLE 18

2-(N-(3-phenylpropionyl)-S-alanyl)-(1S,3S,5S)-2-azabicyclo[3.3.0]octane-3-carboxylic acid $\alpha^{20}_{D}$:−25.2° (c=1.02 in methanol).
Melting point: 180–184° C.

EXAMPLE 19

2-(N-(tert.-butoxycarbonyl)-S-alanyl)-(1S,3S,5S)-2-azabicyclo[3.3.0]octane-3-carboxylic acid $\alpha^{25}_{D}$:−29.3° (c=1 in methanol).

EXAMPLE 20 n-Octyl 2-N-(4-(2-naphthyl)butyryl)-(1S,3S,5S)-2-azabicyclo[3.3.0]octane-3-carboxylate 0.5 g of the carboxylic acid obtained in Example 8 was dissolved in 10 ml of absolute dimethylformamide, then treated at 40° C. with 285 mg of KHCO$_3$ for one hour in the absence of moisture, and then 0.6 ml of n-octyl bromide was added. After 3 hours at 40° C., the reaction was completed. The solution was diluted with water and extracted three times with 20 ml each of ethyl acetate. The organic phase was washed with NaCl solution, dried over MgSO$_4$ and concentrated in vacuo. The crude product thus obtained was purified by column chromatography over silica gel (cyclohexane/ethyl acetate). The yield was 378 mg.

$\alpha^{20}{}_{D}$: −2.4° (c=1.14 in methanol).

The following compounds of Examples 21 and 22 were obtained analogously to the procedure described above in Example 20:

EXAMPLE 21 n-Octyl 2-phenylacetyl-[1S,3S,5S]-2-azabicyclo[3.3.0]-3-octane-carboxylate $\alpha^{25}{}_{D}$: −9.8° (c=1 in methanol).

EXAMPLE 22 n-Octyl 2-(5-phenylvaleryl)-[1S,3S,5S]-2-azabiccylo[3.3.0]octane-3-carboxylate $\alpha^{25}{}_{D}$: −4.0° (c=0.99 in methanol).

EXAMPLE 23

Benzyl 2-(N-(3-phenylpropionyl)-S-alanyl)-(1S,3S,5S)-2-azabicyclo[3.3.0]octane-3-carboxylate a) N-(3-phenylpropionyl)-S-alanine benzyl ester 9.70 g of L-alanine benzyl ester hydrochloride and 6.75 g of 3-phenylpropionic acid were dissolved in 125 ml of dichloromethane, cooled to −5° C., and 37.5 ml of triethylamine are added under N$_2$. After 10 minutes, 45 ml of n-propylphosphonic anhydride (50 % strength in CH$_2$Cl$_2$) are added dropwise to this solution, and the mixture is stirred at −5° C. for one hour and then at room temperature overnight. It was worked up as in Example 1 and, after recrystallization from cyclohexane/ethyl acetate, gave 9.5 g of the desired product of melting point 59–60° C.

b) The benzyl ester obtained in a) was hydrogenated catalytically in 250 ml of ethanol on palladium/carbon.

After removal of the catalyst by filtration and concentration of the filtrate in vacuo, 6.9 g of N-(3-phenylpropionyl)-S-alanine were obtained.

$\alpha^{20}{}_{D}$: −32.9° (c=1.66 in methanol).

c) 3.3 g of the carboxylic acid obtained in b) and 3.65 g of benzyl 2-azabicyclo[3.3.0]octane-3-carboxylate were reacted by the method described in Example 1 with 15 ml of n-propylphosphonic anhydride, worked up as described and isolated. This gave 3.3 g of the desired product.

$\alpha^{20}{}_{D}$: 43 4° (c=1.21 in methanol).

EXAMPLE 24 n-Octyl (1S,3S,5S)-2-azabicyclo[3.3.0]octane-3-carboxylate L(hydrogen tartrate)

15 ml of trifluoroacetic acid were poured at 0° C. over 4.5 g (12.2 mmol) of the BOC compound from Example 10, and the mixture was stirred for 90 minutes. The solvent was evaporated, the residue was taken up in saturated sodium bicarbonate solution, extracted three times with ethyl acetate, the combined extracts were dried and concentrated. This gave 3.1 g of n-octyl (1S,3S,5S)-2-azabicyclo[3.3.0]octane-3-carboxylate.

This ester is dissolved in ether, and a solution of 1.74 g of L-tartaric acid in acetone is added. The precipitate is filtered off with suction to give 2.5 g of the product.

$\alpha^{25}{}_{D}$: −13.6° (c=1 in methanol).

EXAMPLE 25 n-Octyl (1S,3S,5S)-2-azabicyclo[3.3.0]octane-3-carboxylate hydrochloride 16.3 g (150 mmol) of distilled trimethylsilyl chloride are added dropwise at 40° C. to a suspension of 10 g (64 mmol) of (1S,3S,5S)-2-azabicyclo[3.3.0]octane-3-carboxylic acid in 100 ml of distilled n-octanol, and the mixture is stirred at 40° C. overnight. The volatile components are removed on a rotary evaporator, octanol is separated off by short-path distillation in a high vacuum, the distillation residue is taken up in methylene chloride, concentrated and triturated twice with diisopropyl ether. This gives 14.6 g (5%) of the title compound. M.p. 76–78° C.

$\alpha^{25}{}_{D}$: −23.7° (C=1, methanol).

EXAMPLE 26 n-Octyl 2-[(Z)-3-methoxycarbonyl-2-propenoyl]-(1S,3S,5S)-2-azabicyclo[3.3.0]octane-3-carboxylate This compound was obtained analogously to the method described in Example 1 from n-octyl (1S,3S,5S)-2-azabicyclo[3.3.0]octane-3-carboxylate and monomethyl maleate. MS (DCI) =380 (M+1).

EXAMPLE 27 n-Octyl 2-[(Z)-3-n-octyloxycarbonyl-2-propenoyl]-(1S,3S,5S)-2-azabicyclo[3.3.0]octane-3-carboxylate The compound was obtained analogously to the method described in Example 1 from n-octyl (1S,3S,5S)-2-azabicyclo [3.3.0]octane-3-carboxylate and mono-n-octyl maleate.

$\alpha^{25}{}_{D}$: −22.1° (c=1, methanol).

EXAMPLE 28 n-Octyl 2-maleoyl-(1S,3S,5S)-2-azabicyclo[3.3.0]octane-3-carboxylate 1.03 g (2.7 mmol) of the diester described in Example 26 were dissolved in 10 ml of dioxane, a solution of 0.126 g (5.4 mmol) of lithium hydroxide in 10 ml of water was added, and the mixture was stirred at room temperature for three hours. The solution was acidified to a pH of 3, extracted with ethyl acetate, the extract was dried, concentrated, and the crude product purified by column chromatography over silica gel (eluent methanol/methylene chloride 3:97). Yield: 0.5 g of the title compound.

$\alpha^{25}_D = -19.4°$ (c=1, methanol).

EXAMPLE 29 n-Octyl (1S,3S,5S)-2-azabicyclo[3.3.0]octane-3-carboxylate hydrogen maleate

This compound was obtained from n-octyl (1S,3S,5S)-2-azabicyclo-[3.3.0]octane-3-carboxylate and maleic acid in ether/acetone 5:1.

$\alpha^{25}_D = -16.1°$ (c=1 in methanol).

We claim:

1. A compound of the formula I

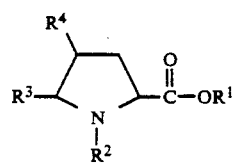

in which

R$^1$ is hydrogen, C$_1$-C$_8$-alkyl, C$_2$-C$_6$-alkenyl, C$_3$-C$_9$-cycloalkyl, amino-C$_1$-C$_4$-alkyl, C$_2$-C$_5$-acylamino-C$_1$-C$_4$-alkyl, C$_7$-C$_{13}$-aroylamino-C$_1$-C$_4$-alkyl, C$_6$-C$_{12}$-aryl-C$_1$-C$_6$-alkyl or C$_6$-C$_{12}$-aryl;

R$^2$ is C$_1$-C$_8$-alkanoyl, C$_6$-C$_{12}$-aryl-C$_1$-C$_6$-alkanoyl, C$_1$-C$_4$-alkoxycarbonyl-C$_1$-C$_7$-alkanoyl C$_6$-C$_{12}$-aryloxycarbonyl-C$_1$-C$_7$-alkanoyl, C$_1$-C$_4$-acyl-C$_2$-C$_6$-alkanoyl, C$_1$-C$_4$-acylamino-C$_1$-C$_6$-alkanoyl or C$_7$-C$_{13}$-aroyl-C$_1$-C$_6$-alkanoyl;

R$^3$ and R$^4$ together with the atoms carrying them form a monocyclic alicyclic or aromatic ring system selected from the group consisting of cyclopentane, cyclopentene, cyclohexane and benzene, and their physiologically acceptable salts, with the exception of compounds in which at the same time R$^1$ is hydrogen, benzyl or n-octyl, R$^2$ is tert.-butoxycarbonyl and R$^3$ and R$^4$ together with the atoms carrying them form a cyclopentane or cyclopentene ring and compounds in which R$^2$ is α-acylamino-C$_1$-C$_6$-alkanoyl.

2. A compound of the formula I as claimed in claim 1, wherein said compound is benzyl 2-N-(5-phenylvaleryl)-(1S,3S,5S) -2-azabicyclo[3.3.0]octane-3-carboxylate.

3. A pharmaceutical preparation containing an active amount of a compound of the formula I as claimed in claim 1, or a physiologically acceptable salt thereof and a physiologically safe carrier.

4. A process for the treatment and prophylaxis of cognitive dysfunctions, which comprises administering an active amount of a compound of the formula I as claimed in claim 1, or a physiologically acceptable salt thereof.

* * * * *